United States Patent [19]
Ishikawa et al.

[11] Patent Number: 5,883,691
[45] Date of Patent: Mar. 16, 1999

[54] PUPIL MEASURING SYSTEM AND ALZHEIMER'S DISEASE DIAGNOSING SYSTEM

[75] Inventors: Norio Ishikawa; Hidehiro Hosaka, both of Tokyo; Shigeaki Sonoda, Kanagawa, all of Japan

[73] Assignee: Nihon Kohden Corporation, Tokyo, Japan

[21] Appl. No.: 649,757

[22] Filed: May 15, 1996

[30] Foreign Application Priority Data

May 15, 1995 [JP] Japan .................................. 7-115848

[51] Int. Cl.⁶ .................................................. A61B 3/10
[52] U.S. Cl. ................................... 351/221; 351/205
[58] Field of Search ................................ 351/221, 211, 351/200, 205, 203, 206, 246; 359/407; 1/419; 128/745

[56] References Cited

U.S. PATENT DOCUMENTS 4,850,691  7/1989  Gardner et al. ..................... 351/221
5,617,872  4/1997  Scinto et al. ....................... 128/745

FOREIGN PATENT DOCUMENTS 2690329  10/1993  France .
9603070   2/1996   WIPO .

OTHER PUBLICATIONS

Medical & Biological Engineering & Computing, vol. 30; No. 5; Sep. 1992; Stevenage, GB; pp. 487–490, XP000323414, D.P. Jones et al.: "Pupillometer for Clinical Applications Using Dual 256–Element Linear CCD Arrays". Science, vol. 266; no. 5187; Nov. 11, 1994, US; pp. 1051–1054, XP000576055, L.F.M. Scinto et al "A Potential Noninvasive Neurobiologival Test for Alzheimer's Disease".

Primary Examiner—Hung Xuan Dang
Attorney, Agent, or Firm—Sughrue, Mion, Zinn, Macpeak & Seas, PLLC

[57] ABSTRACT

Light sources illuminate eyes in a predetermined cycle using the pulse of light. Video cameras are directed to the eyes, and a video signal of the pupil is output. This video signal is output to a digital computer via video control units, a multiplexer, and an analog-to-digital converter. The digital computer detects the size of the pupil by processing an input video signal.

12 Claims, 9 Drawing Sheets

PUPIL MEASURING SYSTEM AND ALZHEIMER'S DISEASE DIAGNOSING SYSTEM

BACKGROUND OF THE INVENTION

1. Field of the Invention

The present invention relates to a pupil measuring system for measuring a pupil diameter and a system for diagnosing Alzheimer's dementia (Alzheimer's disease) by measurement of the size of a pupil.

2. Related Art

It is said that about one million patients suffer from senile dementia in Japan. About half those patients are affected by cerebrovascular dementia, and the rest of them are affected by Alzheimer's disease. No early diagnosing method was conventionally available for Alzheimer's patients. Medicines for delaying the progress of Alzheimer's disease have now been developed, which makes it possible to delay the progress of the disease if Alzheimer's disease can be diagnosed early. For this reason, the method for early diagnosis of Alzheimer's disease has long been expected.

A method for early diagnosis of Alzheimer's disease was reported in a US Journal entitled SCIENCE (VOL. 266, 11 NOV., 1994), which enables the early diagnosis of Alzheimer's disease by dropping a pupil dilating dilution into an eye, and by measuring the area of a resultantly dilated pupil or the magnification of the pupil diameter. However, a diagnosing system employing this method is not available yet.

The following problems were encountered as a result of an attempt to build the diagnosing system of this type by combining together conventional units, such as, a pupil photographing unit which measures the area of a pupil or the magnification of a pupil diameter and a data analyzing unit which analyzes data obtained by the pupil photographing unit.

In the conventional pupil photographing unit, an eye is exposed to continuous light using a continuously illuminating device as a photographing device. The pupil is stimulated by flashing light, and the area of the pupil or changes in the pupil diameter obtained as a result of the lapse of several seconds after the stimulation of the pupil. The above described method for early diagnosis of Alzheimer's disease requires the measurement of changes in the pupil size over a long period of time, e.g., 30 minutes to one hour. However, the eye often moves during the course of the measurement which is continued over such a long period time, thereby resulting in eye deflections. The eye deflections make it difficult to accurately measure the area of the pupil or the pupil diameter.

To reproduce an image on a monitor by processing a signal output from a video camera, the speed of an electric shutter is usually set to a standard speed, that is, a rate of 1/60 sec. Data for two fields are obtained from the data which the video camera outputs for every one screen, that is, at an interval of 1/60 sec. One screen (one frame) is formed on a monitor screen by means of the data. If the eye moves quickly, displacements arise even in the image of the pupil for two fields at an interval of 1/60 sec. This problem will be described in a more detailed manner.

Figure 9:
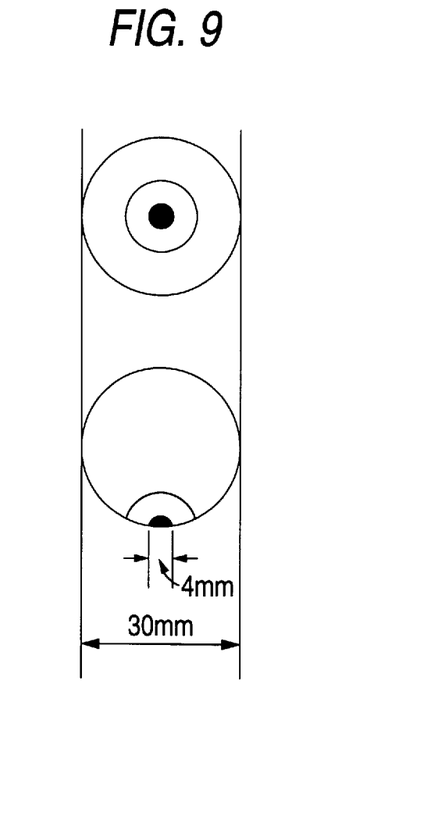
FIG. 9 is a schematic representation for describing a travel speed of the pupil center as a result of eye movement.

Eye movement is generally divided into two types, i.e., a slow phase and a quick phase. The slow phase designates the slow movement of the eye, and the quick phase designates the quick movement of the eye. The quick phase represents, for example, the momentary return of the eyes after they have followed a train passing a railway crossing from left to right. Contrary to this, the slow phase means the movement of the eyes as they are following the train from left to right. It is said that a rotating speed of the eye in the quick phase is 300 to 500 degrees/sec. Provided that the rotating speed of the eye is 500 degrees/sec., the front surface of the eye moves together with a pupil in the following manner. In the example, the diameter of the eye is assumed to be 30 mm, as shown in FIG. 9, and the speed of the electronic shutter is set to a standard period of 1/60 sec.

(1) A traveling speed of the pupil center is $\pi \times 30 \times (500/360)$ mm/sec.=about 131 mm/sec.

(2) A travel distance of the pupil center during a period of 1/60 sec. is (131 mm/sec)×(1/60 sec.)=about 2.2 mm.

Figure 10:
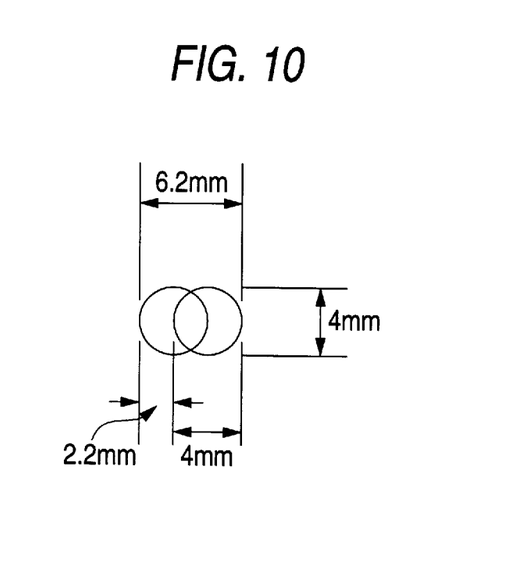
FIG. 10 is a schematic representation for describing displacements of the pupil.

(3) Displacements of the subject, i.e., the pupil, are as follows:

The pupil commonly measures approximately 3–5 mm in diameter. In this event, the pupil is assumed to measure 4 mm, as shown in FIG. 9. The pupil having a diameter of 4 mm travels 2.2 mm during a period of 1/60 sec, which in turn results in a substantially elliptical image having a longer radius of about 6.2 mm and a shorter radius of about 4 mm, as shown in FIG. 10. An apparent area of the image is about more than 150% of the true area. Hence, there arises an error of more than 50%. For this reason, it becomes impossible to accurately measure the area of the pupil or the pupil diameter.

To prevent such a problem, it may be possible to form one screen (one frame) on the monitor screen by using the data of the identical field obtained from the video camera twice while the release period of the electronic shutter remains set to a standard period of 1/60 sec. Even in the case of this method, the image moves during one field having a period of 1/60 sec. if the eye is exposed to continuous light, thereby resulting in a blurred pupil image.

Alternatively, it may be possible to use intensive and continuous light while the speed of the electronic shutter is set to a small period of time, e.g., 1/1000 sec. According to this method, on the assumption that the rotating speed of the eye is 500 degrees/sec. and the diameter of the eye is 30 mm, the pupil center travels at a speed of about 131 mm/sec along the surface of the eye. Hence, the travel distance of the pupil center during a period of 1/1000 sec. is (131 mm/sec.)×(1/1000 sec.)=0.131 mm. Assuming that the pupil diameter is 4 mm, a ratio of the apparent area of the pupil to the true area of the same is $4.131^2/4^2=1.067$ (times). The error of the area of the pupil is reduced to about 6.7%.

However, if the eye is continuously exposed to intensive light, there is a risk of damaging the cornea of the eye. For this reason, this second method is not practical. Conversely, if the speed of the electronic shutter is set to a very short time, e.g., 1/1000 sec., and weak light is continuously used, the image will become dark, which makes it difficult to analyze the image. The dark image is not suitable for measuring the pupil size.

Figure 7:
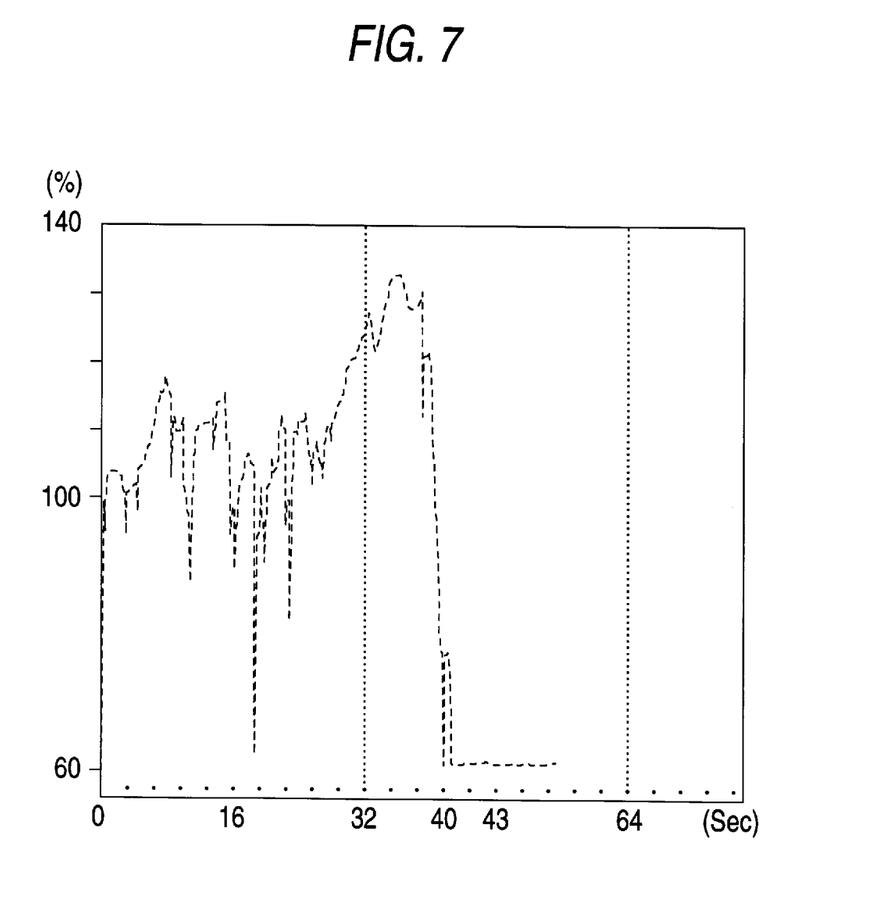
FIG. 7 is a plot which shows variations in the values obtained as a result of measurement of the area of the pupil when they are not averaged.
Figure 8:
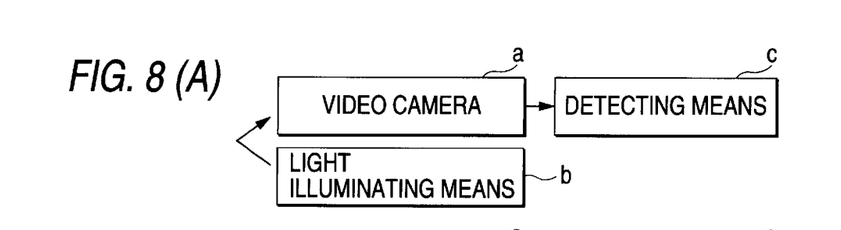
FIGS. 8A to 8E are diagrams schematically showing configurations of the Alzheimer's disease diagnosing system of the present invention.

The conventional data analyzing unit for analyzing data obtained by the pupil photographing unit is designed to directly use data relating to the size of the pupil which are obtained at predetermined intervals of time. However, the eye itself is reduced or increased in size all the time. Thus, constant changes of this type in the area of the pupil are ignored in the conventional data analyzing unit, which in turn results in errors. For example, on the assumption that the area of the pupil obtained as a result of the first measurement is 100%, and that the area of the pupil is then measured for 40 seconds at every 0.2 seconds, the area of the pupil changes all the time, as shown in FIG. 7. The area changes in as much as a range of about 100–130%. If the minor movement of the eye is measured for a short period of time, no problems arise. However, this method is not desirable to measure the overall changes in the pupil size over a long period of time, and data obtained as a result of such a measurement make it difficult to carry out a correct diagnosis of Alzheimer's disease.

SUMMARY OF THE INVENTION

The present invention is conceived to solve such a problem that the combination of the conventional units makes it impossible to implement diagnosis of Alzheimer's disease which requires a long period of time to carry out measurement. The primary object of the present invention is to provide a system which is capable of diagnosing Alzheimer's disease by obtaining clear image data on a pupil which are used for accurately measuring the size of a pupil, and by averaging data obtained as a result of the measurement of the pupil diameter even if the data change slightly.

According to a first aspect of the present invention, there is provided a pupil measuring system comprising a video camera disposed so as to face a patient's eyes, illuminating means for irradiating the pulse of image pick-up light of the video camera in a predetermined cycle, and detecting means for detecting a quantity relating to a pupil size for a plurality of time points, e.g. the measurement for one minute is carried out once every seven minutes up to a total of five times, by processing a video signal output from the video camera.

According to a second aspect of the present invention, the pupil measuring system, as defined in the first aspect, further comprises mean value calculating means for obtaining a predetermined number of subdivided quantities relating to the pupil size for the respective time points detected by the detecting means, as well as calculating a mean value of the subdivided quantities.

According to a third aspect of the present invention, there is provided an Alzheimer's disease diagnosing system comprising a video camera disposed so as to face a patient's eye, illuminating means for irradiating the pulse of image pick-up light of the video camera in a predetermined cycle, detecting means for detecting a quantity relating to the pupil size for a plurality of time points by processing the video signal output from the video camera, and determination means for determining whether or not the patient is diagnosed as being affected with Alzheimer's disease on the basis of the quantity detected by the detecting means.

According to a fourth aspect of the present invention, there is provided an Alzheimer's disease diagnosing system comprising a video camera disposed so as to face a patient's eye, illuminating means for irradiating the pulse of image pick-up light of the video camera in a predetermined cycle, detecting means for detecting a quantity relating to the pupil size for a plurality of time points by processing the video signal output from the video camera, mean value calculating means for obtaining a predetermined number of subdivided quantities relating to the pupil size for the respective time points detected by the detecting means, as well as calculating a mean value of the subdivided quantities, and determination means for determining whether or not the patient is diagnosed as being affected with Alzheimer's disease on the basis of the mean quantity relating to the pupil size calculated by the mean value calculating means.

According to a fifth aspect of the present invention, there is provided an Alzheimer's disease diagnosing system comprising a video camera disposed so as to face a patient's eyes, illuminating means for irradiating image pick-up light of the video camera, detecting means for detecting a quantity relating to the pupil size for a plurality of time points by processing the video signal output from the video camera, change rate calculating means for calculating a rate of change of the pupil size in at least one predetermined interval between time points on the basis of the quantity detected by the detecting means, and determination means for determining whether or not the patient is diagnosed as being affected with Alzheimer's disease on the basis of the rate of change of the quantity for the pupil size calculated by the change rate calculating means.

In the pupil measuring system as defined in the first aspect of the present invention, the patient's eye is exposed to the pulse of image pick-up light by means of the illuminating means. The video signal output from the video camera is a video signal of the pupil exposed to the pulse of light. The detecting means detects the quantity relating to the pupil size for a plurality of time points by processing the video signal.

In the pupil measuring system as defined in the second aspect of the present invention, the mean value calculating means calculates a predetermined number of subdivided quantities relating to the pupil size for the respective time points detected by the detecting means, as well as calculating a mean value of the subdivided quantities.

In the Alzheimer's disease diagnosing system as defined in the third aspect of the present invention, the illuminating means irradiates the pulse of image pick-up light to the patient's eye. The video signal output from the video camera is a video signal of the pupil exposed to the pulse of light. The detecting means detects a quantity relating to the pupil size for a plurality of time points by processing the video signal output from the video camera. The determination means determines whether or not the patient is diagnosed as being affected with Alzheimer's disease on the basis of the quantity detected by the detecting means.

In the Alzheimer's disease diagnosing system as defined in the fourth aspect of the present invention, the illuminating means irradiates the pulse of image pick-up light to the patient's eye. The video signal output from the video camera is a video signal of the pupil exposed to the pulse of light. The detecting means detects a quantity relating to the pupil size for a plurality of time points by the video signal. The mean value calculating means calculates a predetermined number of subdivided quantities relating to the pupil size for the respective time points detected by the detecting means, as well as calculating a mean value of the subdivided quantities. The determination means determines whether or not the patient is diagnosed as being affected with Alzheimer's disease on the basis of the mean quantity relating to the pupil size calculated by the mean value calculating means.

In the Alzheimer's disease diagnosing system as defined in the fifth aspect of the present invention, the illuminating means irradiates image pick-up light to the patient's eye. The video signal output from the video camera is a video signal of the pupil exposed to the light. The detecting means detects a quantity relating to the pupil size for a plurality of time points by processing the video signal. The change rate calculating means calculates a rate of change of the pupil size in at least one predetermined interval between time points on the basis of the quantity detected by the detecting means. The determination means determines whether or not the patient is diagnosed as being affected by Alzheimer's disease on the basis of the rate of change of the quantity for the pupil size calculated by the change rate calculating means.

DETAILED DESCRIPTION OF THE PREFERRED EMBODIMENTS

Figure 1:
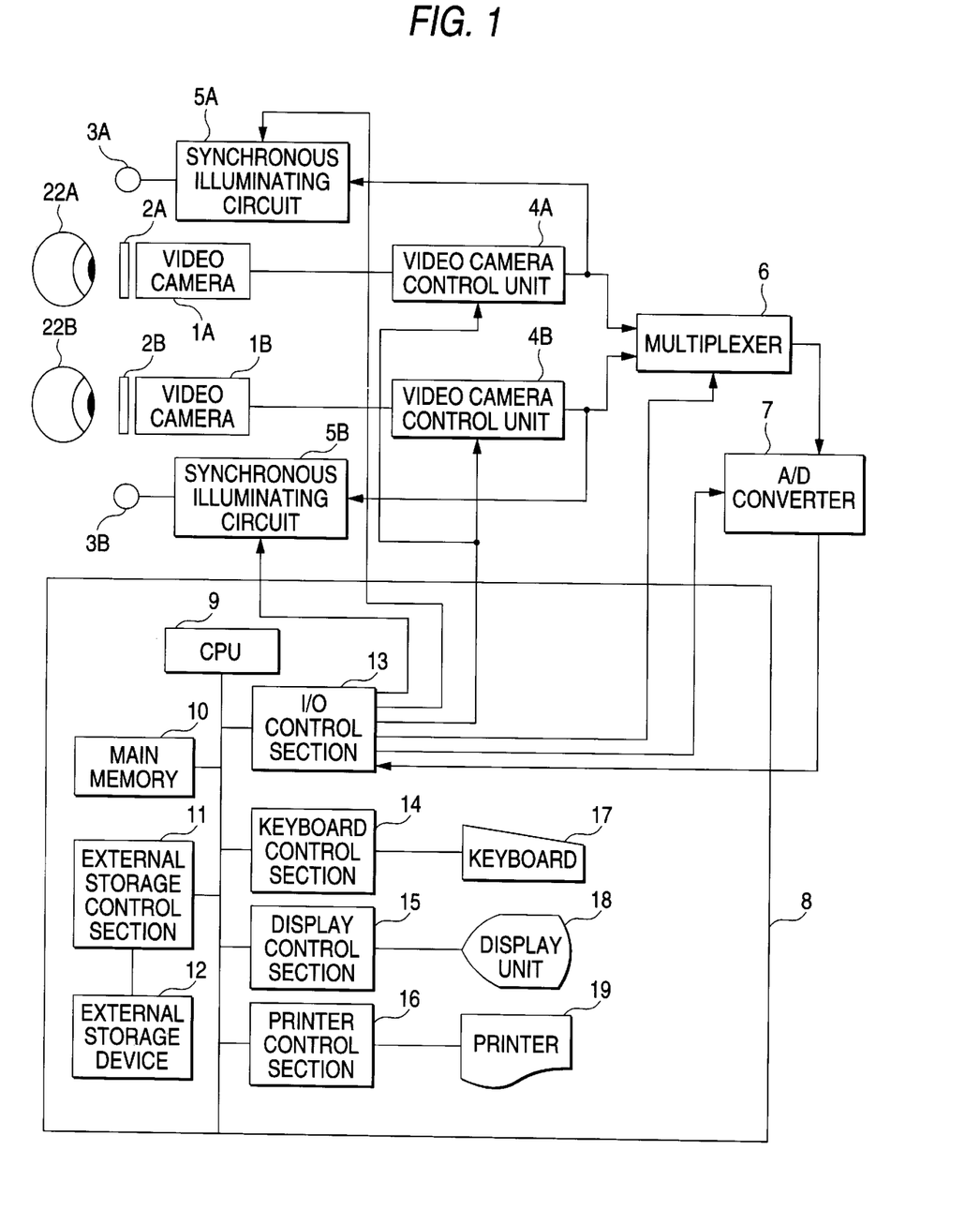
FIG. 1 is a schematic diagram which shows the overall configuration of an Alzheimer's disease diagnosing system according to a first embodiment of the present invention.

With reference to FIG. 1, the overall configuration of a pupil measuring system according to a first embodiment of the present invention. Each of a pair of video cameras 1A and 1B is made up of an optical lens and an image pick-up element. A subject is converted into a two-dimensional image, and that image is divided into a plurality of pixels. The pixels are respectively converted into an electrical signal, and the signal is output in a predetermined order. In the present embodiment, the image pick-up element is a CCD. An infrared ray is used in the present embodiment, and hence visible light cut-off filters 2A and 2B are attached to the respective front surfaces of the video cameras 1A and 1B in order to eliminate visible light which becomes noise. Light sources 3A and 3B are respectively disposed in the vicinity of the video cameras 1A and 1B. The light sources 3A and 3B are LEDs which illuminate infrared rays.

Figure 2:
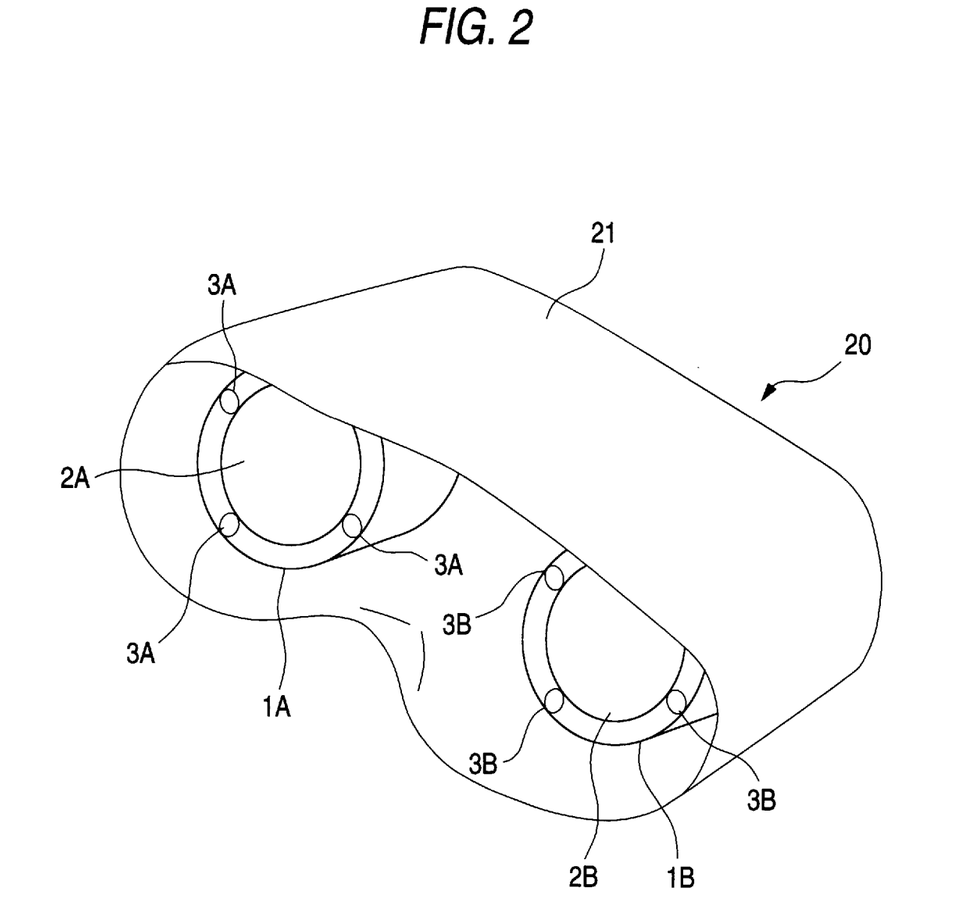
FIG. 2 is an external view which shows the appearance of goggles used in the first embodiment.

The video cameras 1A and 1B, the visible light cut-off filters 2A and 2B, and the light sources 3A and 3B constitute goggles 20, as shown in FIG. 2. Specifically, these elements are attached to a goggle main body 21, whereby they are integrated together. Each of the light sources 3A and 3B comprises a plurality of LEDs, and they are disposed around the respective front surfaces of the video cameras 1A and 1B.

Turning again to FIG. 1, a pair of video camera control units 4A and 4B control actuation timing of electronic shutters of the video cameras 1A and 1B, namely, they control the periodicity of exposure, exposure time, and the outputs of the video cameras 1A and 1B. As a result, a composite video signal, which comprises the video signals output from the video cameras 1A and 1B and synchronizing signals, is output. Synchronous illuminating circuits 5A and 5B determine blinking timing of the light sources 3A and 3B on the basis of the synchronizing signals of the composite video signal output from the video camera control units 4A and 4B.

A multiplexer 6 allows the video camera control units 4A and 4B to selectively produce an output. An analog-to-digital converter 7 converts the output from the multiplexer 6 into a digital signal.

A digital computer 8 controls the video camera control units 4A and 4B, the synchronous illuminating circuits 5A and 5B, the multiplexer 6, and the analog-to-digital converter 7, as well as processing the data output from the analog-to-digital converter 7. The digital computer 8 employed in the present embodiment is a personal computer.

The digital computer 8 is provided with a CPU 9; main memory 10 connected to the CPU 9; an external storage control section 11; an I/O control section 13; a keyboard control section 14; a display control section 15; a printer control section 16; an external storage device 12 which is connected to each of the external storage control section 11, the keyboard control section 14, the display control section 15, and the printer control section 16; a keyboard 17; a display unit 18; and a printer 19. The CPU 9 supervises and controls the overall digital computer 8, as well as controlling each part of the system and processing data on the basis of a program stored in the main memory 10. The main memory 10 consists of ROM (read only memory) and RAM (read/write memory). The ROM holds programs and data which are important for the CPU 9 to execute the program read into the RAM from the external storage device 12. Data or results of data processing, which become important for the CPU 9 to process the data, are written into the RAM. The external storage device 12 holds various programs and data items. In the present embodiment, it holds the program shown in FIG. 3.

The external storage control section 11 controls the reading of data from, and the writing of data into, the external storage device 12 according to an instruction from the CPU 9. The I/O control section 13 controls the exchange of data between the digital computer and external devices, as well as controlling the sending of a control signal to, and the receipt of a control signal from, the external devices.

The keyboard 17 has a plurality of keys and outputs a corresponding signal when any one of the keys is pressed. The keyboard control section 14 controls signals output from the keyboard 17 and stores them in the main memory 10 according to the instruction from the CPU 9. The display unit 18 visually displays the data which the unit receives on a display screen. In the present embodiment, the display unit 18 is a CRT. The display control section 15 displays the data stored in the main memory 10 on the display unit 18 according to the instruction from the CPU 9. The printer 19 prints the data which the printer receives on paper. The printer control section 16 controls the printer 19 according to the instruction from the CPU 9, and the printer 19 carries out a printing operation based on the data stored in the main memory 10.

The pupil measuring system of the present embodiment is made up of the video cameras 1A and 1B, the light sources 3A and 3B, the synchronous illuminating circuits 5A and 5B, the video camera control units 4A and 4B, the multiplexer 6, the analog-to-digital converter 7, and the means of the digital computer 8 that has the function of detecting the pupil size by processing the video signal. Of these elements, the video cameras 1A and 1B correspond to video cameras, and illuminating means are made up of the light sources 3A and 3B and the synchronous illuminating circuits 5A and 5B.

The detecting means is made up of the video control units 4A and 4B, the multiplexer 6, the analog-to-digital converter 7, and the means of the digital computer 8 that has the function of detecting a pupil size by processing a video signal.

In the present embodiment, the Alzheimer's disease diagnosing system is constituted of the elements that form the pupil measuring system and the means of the digital computer 8 that has the function of determining whether or not the patient is diagnosed as being affected by Alzheimer's disease on the basis of the pupil size. The elements constituting the pupil measuring system respectively correspond to the elements of the previously described present embodiment. Of the digital computer 8, the means, which has the function of determining whether or not the patient is diagnosed as being affected with Alzheimer's disease on the basis of the pupil size, corresponds to the determination means.

With reference to a flowchart shown in FIG. 3 and a timingchart shown in FIGS. 4A to 4F, the operation of the Alzheimer's disease diagnosing system will now be described. The description is based on the assumption that the program represented by the flowchart shown in FIG. 3 is read from the RAM of the main memory 10 as a result of the operation of the keyboard 17.

Figure 4A:
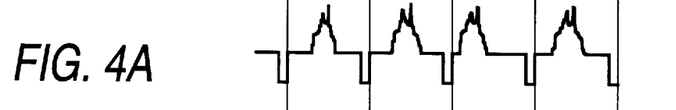
FIG. 4A to 4F are timingchart for describing video signals of a right eye and a left eye, fetching timing of a sychronizing signal and a field image.
Figure 4B:
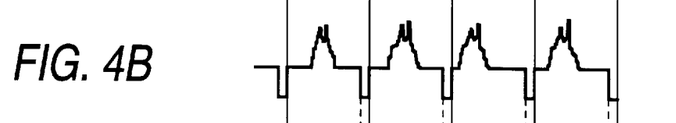
Figure 4C:
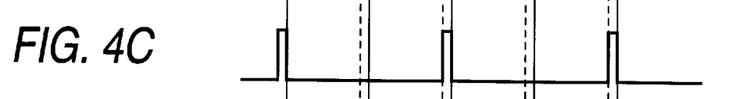
Figure 4D:
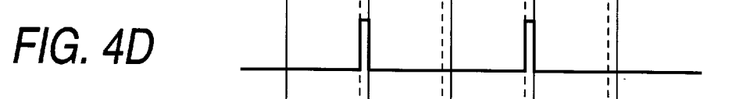
Figure 4E:
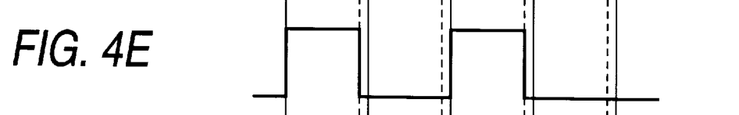
Figure 4F:
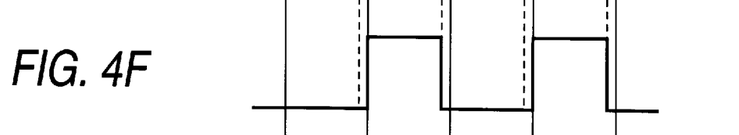

(1) Before dropping a pupil dilating agent into an eye:

A patient first prepares for the measurement of the pupil by wearing the goggles 20 shown in FIG. 2 in step 301. In this event, a left eye 22A is situated in front of the video camera 1A, and a right eye 22B is situated in front of the video camera 1B, as shown in FIG. 1. The power of the system is turned on to start the measurement in step 302, and then the measurement of the pupil is started in step 303. As shown in FIGS. 4A and 4B, composite video signals of the right eye and the left eye are output to the video camera control units 4A and 4B. The synchronous illuminating circuit 5A outputs a pulse signal having, e.g., a width of 1 msec shown in FIG. 4C, to the light source 3A in synchronism with a synchronizing signal of an output of the video camera control unit 4A. The light source 3A illuminates over the period of time specified by the pulse signal. Similarly, the synchronous illuminating circuit 5B outputs a pulse signal having, e.g., a width of 1 msec shown in FIG. 4D, to the light source 3B in synchronism with a synchronizing signal of an output of the video camera control unit 4B. The light source 3B illuminates over the period of time specified by the pulse signal. The electronic shutters of the video cameras 1A and 1B are designed so as to open at the same timing when the synchronous illuminating circuits 5A and 5B cause the light sources 3A and 3B to illuminate. According to the timing shown in FIGS. 4E and 4F, the multiplexer 6 allows the video camera control units 4A and 4B to alternately send an output to the analog-to-digital converter 7. Consequently, the outputs from the video camera control units 4A and 4B are alternately converted into digital data for every one field. The thus converted digital data are sent to the digital computer 8.

Figure 3:
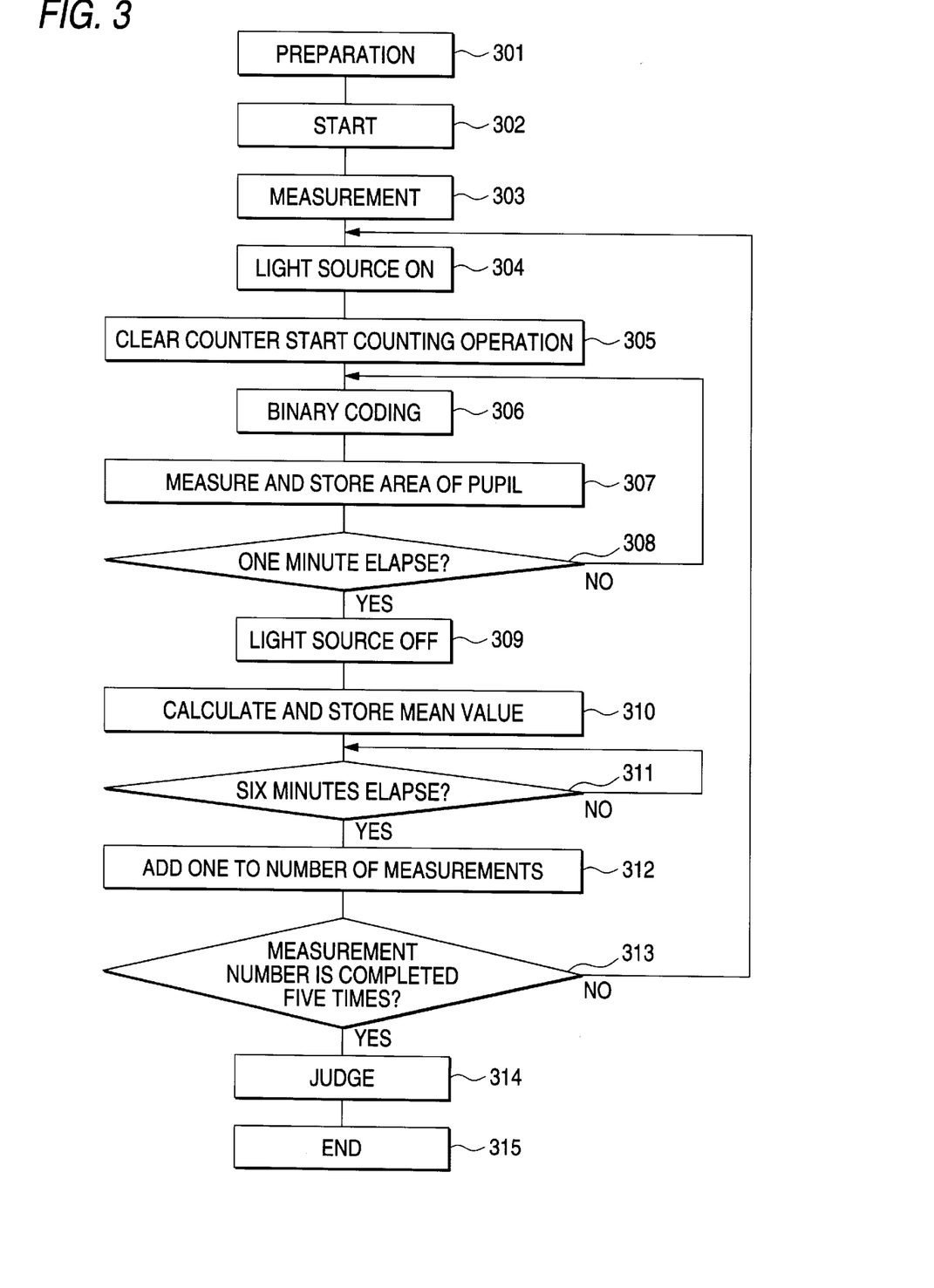
FIG. 3 is a flowchart for describing the operation of the Alzheimer's disease diagnosing system according to the first embodiment of the present invention.

On the other hand, the CPU 9 of the digital computer 8 starts a first counting operation in step 305 shown in FIG. 3. The CPU 9 also fetches a video signal for every one field of the right and left video signals output from the analog-to-digital converter 7. The thus fetched video signals are stored in the RAM of the main memory 10. The CPU 9 proceeds to step 306, and profiles of the pupil images are clearly formed by binary-coding the fetched field of the right and left video signals. The CPU 9 then proceeds to step 307, and the area of each of the pupils is calculated from the right and left pupil images. The thus calculated areas are stored in the RAM of the main memory 10. The CPU 9 then proceeds to step 308. The measurement of the area of the pupil is repeatedly carried out until one minute elapses from the start of the first counting operation. If one minute has already elapsed, the processing proceeds to step 309. At this time, the light source is turned off to suspend the illumination of the pulse of light.

The CPU 9 subsequently proceeds to step 301, and a mean value of the area of the pupil is calculated for each of the left and right pupils. The thus calculated mean values are stored in the RAM of the main memory 10. If it has been judged in step 307 that one minute has not elapsed yet, the CPU 9 returns to step 306. After the processing of step 310, the CPU 9 waits for a measurement start instruction entered as a result of the operation of the keyboard 17. An examiner takes the goggles 20 off from the patient and drops a pupil dilating agent into the patient's eyes. The patient wears the goggles 20 again. On checking that the patient is properly wearing the goggles 20, the examiner enters the measurement start instruction by operating the keyboard 17.

(2) After the pupil dilating agent has been dropped into the eyes:

When the CPU 9 receives the measurement start instruction in step 312, as shown in FIG. 3, one is added to the number of measurements, and the first measurement of the pupil size is started. In other words, the processing returns to previously described step 304, and the measurement of the area of the pupils after the pupil dilating agent has been dropped into the eyes and the storage of results of the measurement are started.

The measurement of the pupil after the dropping of the pupil dilating agent into the eyes is programmed such that the measurement for repeating steps 306 and 307 for one minute is carried out once every seven minutes up to a total of five times. Consequently, the results obtained by measuring the area of the pupil several times in one minute are averaged in step 310, and the thus obtained mean value is stored. The CPU 9 carries out a counting operation in step 311 and waits six minutes. Upon confirmation of the lapse of six minutes as a result of the counting operation, one is added to the number of measurements in step 312. Thus, the next measurement is started. This measurement is repeated until it is confirmed in step 313 that the measurement is completed five times, that is, until 30 minutes lapse after the dropping of the pupil dilating agent.

Figure 5:
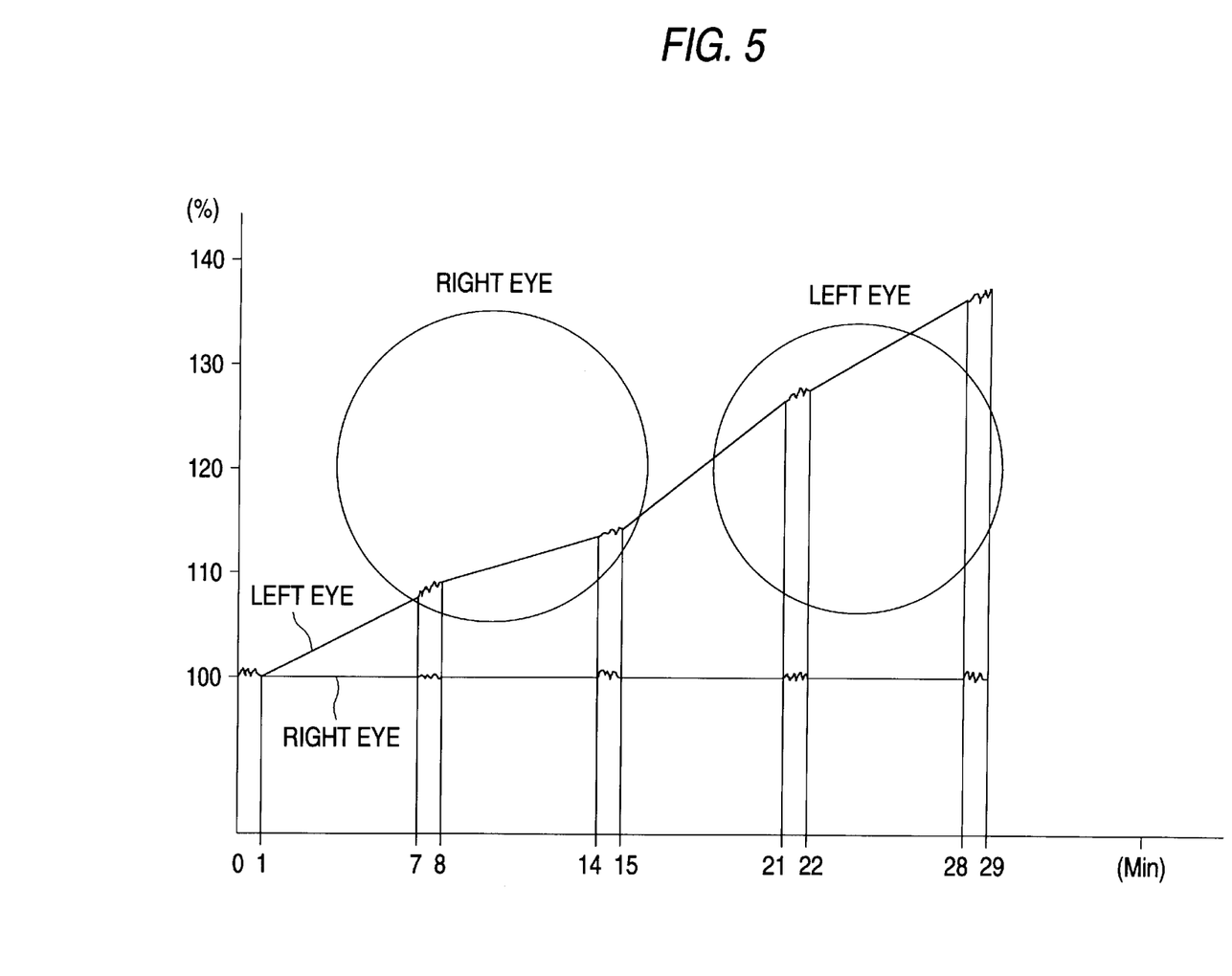
FIG. 5 is a plot which shows one example of data displayed on a display unit according to the embodiment of the present invention.

The CPU 9 is programmed to hold the data averaged in step 310 as well as to plot a graph on the screen of the display unit 17 by calculating a ratio of the areas of the pupil before and after the dropping of the pupil dilating agent, as shown in FIG. 5. In addition to the data on the left eye into which the pupil dilating agent has been dropped, the data on the right eye into which the pupil dilating agent has not yet been dropped are simultaneously displayed in order to facilitate a comparison between them, as shown in FIG. 5. Further, in the same drawing, the images of the left and right eyes themselves are displayed so as to overlap with each other, which helps the examiner to observe changes in the size of the pupils.

In step 410, the CPU 9 determines whether or not the patient is affected with Alzheimer's disease on the basis of the results of the measurement. The determination is carried out in the following manner.

To begin with, the CPU 9 obtains the minimum value of the averages obtained as a result of the measurement carried out in the last one minute (the fifth measurement). If the minimum value is in excess of 113 (%), it is judged that the patient is affected with Alzheimer's disease. If the minimum value is not in excess of 113 (%), it is judged that the patient is not affected with Alzheimer's disease. These results are displayed on the display unit 18.

The reasons why such a determination is made will now be described. When the one-minute measurement is carried out five times, the data as shown in FIG. 5 are displayed on the display screen of the display unit 18, as previously described. Twenty nine minutes have already elapsed at the end of the last one-minute measurement after the pupil dilating agent has been dropped into the eye. As is evident from FIG. 6, the rate of dilation of the pupil of Alzheimer's patient is different from that of an individual who is not affected with Alzheimer's disease (see the previously described report in the journal entitled SCIENCE). In other words, the rate of dilation of the pupil of Alzheimer's patient is in excess of 113% when 29 minutes have elapsed after the pupil dilating agent has been dropped into the eye.

Changes in the patient's pupil are displayed on the display unit in real time in the present embodiment, which allows the examiner to immediately determine the patient's condition. Contrary to this, it may be possible to record a video signal output of the video camera obtained as a result of the measurement using a video recorder, and the recorded signal is analyzed later. Even in this case, the measurement is carried out for one minute several times at an interval of six minutes. The video recorder is constantly held in a recording state throughout the time period over which the measurement is carried out. The light source is illuminated in a certain cycle (e.g., a cycle of $1/60$ sec.) only during the course of the measurement (e.g., one minute). With this arrangement, the lapse of time required by the measurement becomes evident by playing a recording, which in turn facilitates the analysis of the measurement. Further, the Alzheimer's disease diagnosing system of this embodiment does not cause the eye to expose to light for a long period of time, and hence the cornea of the eye damaged as a result of exposure to light for a long period of time does not occur. Noticeable effects are obtained particularly in the case of infrared rays.

Although the area of the pupil is measured at the time of the measurement of the pupil size in the present embodiment, it may be possible to measure the pupil diameter.

The visible light cut-off filter is provided in front of the front surface of the video camera, and infrared rays are used as image pick-up light in the present embodiments. As a result, a large amount of light which is unnecessary for the measurement does not enter the video camera even when the patient takes off the goggles. For this reason, it is possible to accurately measure the pupil diameter or the area of the pupil.

In this embodiment, Alzheimer's disease was diagnosed by observing the magnification of the pupil resulting from the lapse of about 30 minutes after the pupil dilating agent was dropped into the eye. However, it is originally impossible to measure the eyes of the patient affected by Alzheimer's disease for a long period of time, which results in an inaccurate diagnosis.

Figure 6:
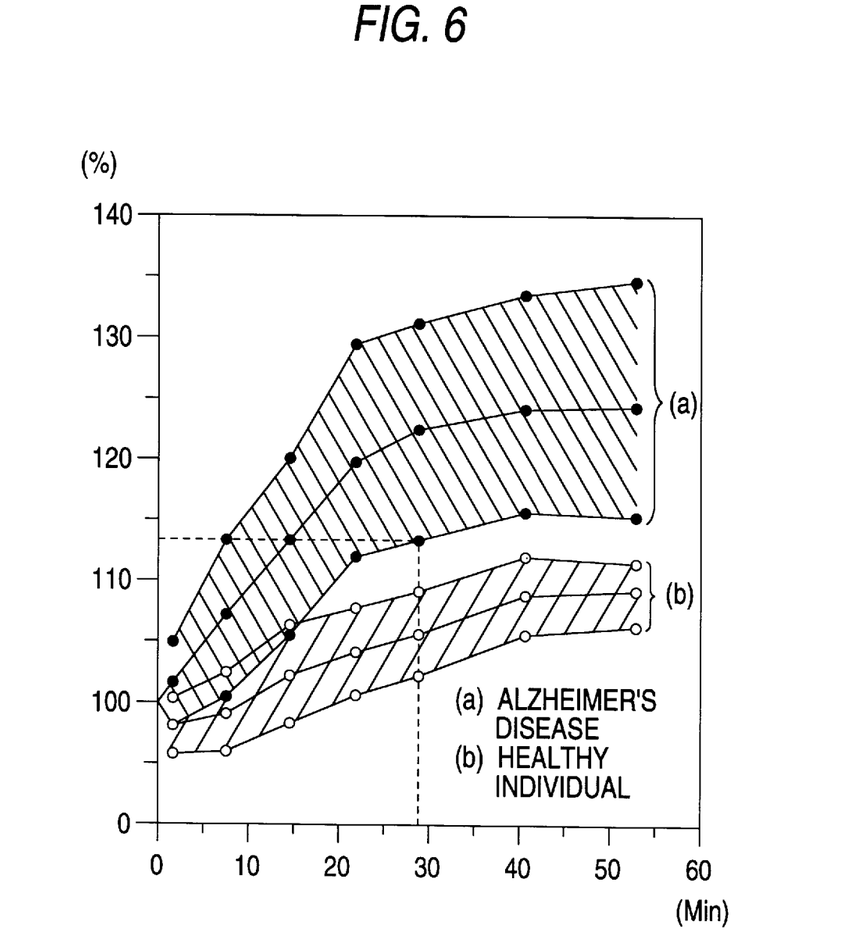
FIG. 6 is a plot for describing changes in the area of a pupil by comparing a patient affected with Alzheimer's disease to an individual without Alzheimer's disease.

To prevent this problem, an Alzheimer's disease diagnosing system according to a second embodiment of the present invention is designed so as to carry out a diagnosis with attention being given to the fact that the area of the pupil or the magnfication (the rate of change) of the pupil diameter of Alzheimer's patients is originally considerably large as is evident from a plot shown in FIG. 6. Specifically, when the inclination of a line between the result of the first measurement (the rate of dilation) and the result of the second measurement (the rate of dilation) shown in FIG. 5 is in excess of a predetermined value, the diagnosis of Alzheimer's disease is carried out. By virtue of the second embodiment, it becomes possible to quickly carry out measurement without putting a physical burden on the patient in a short period of time.

The pupil is measured for a plurality of preset time points in the present embodiment. A mean value of the results of the measurement is calculated, and the inclination of a line between the measurements is obtained on the basis of the mean value. Therefore, it is possible to obtain a very reliable value.

According to a first aspect of the present invention, the eye is exposed to the pulse of image pick-up light, and therefore it is possible to obtain the necessary amount of light to photograph the eye even in the case of a short exposure time. For this reason, if the eye moves during the course of the measurement, a clear pupil image is obtained, which permits the accurate measurement of the pupil size.

According to a second aspect of the present invention, a mean value of the sizes of the pupil obtained as a result of the measurements. Accordingly, if some of them include errors, it is possible to substantially accurately measure the pupil size without an influence of the errors by and large.

According to a third aspect of the present invention, if the eye moves during the course of the measurement, a clear pupil image is obtained, which makes it possible to accurately determined whether or not the patient is affected with Alzheimer's disease.

According to a fourth aspect of the present invention, even if some of the sizes of the pupil obtained as a result of the measurements include large errors, it is still possible to accurately determine whether or not the patient is affected with Alzheimer's disease.

According to a fifth aspect of the present invention, it is possible to diagnose Alzheimer's disease in a short period of time.

What is claimed is:

1. A pupil measuring system comprising:
   a video camera, disposed so as to face a patient's eye, which outputs a video signal;
   illuminating means for illuminating the patient's eye;
   detecting means for detecting, at a plurality of time points, a value representing a pupil size based upon said video signal output from said video camera; and
   mean value calculating means for obtaining a predetermined number of values respectively representing the pupil size for said time points detected by said detecting means, and for calculating a mean value of said values.

2. A pupil measuring system as claimed in claim 1, wherein said illuminating means irradiates a pulse of light in a predetermined cycle.

3. An Alzheimer's disease diagnosing system, comprising:
   a video camera disposed so as to face a patient's eye;
   illuminating means for illuminating the patient's eye;
   detecting means for detecting, at a plurality of time points, a value representing a pupil size based upon said video signal output from said video camera;
   mean value calculating means for obtaining a predetermined number of values respective representing the pupil size for said time points detected by said detecting means, and for calculating a mean value of said values; and determination means for determining whether the patient is affected with Alzheimer's disease on the basis of said means value.

4. An Alzheimer's disease diagnosing system as claimed in claim 3, wherein said illuminating means irradiates a pulse of light in a predetermined cycle.

5. An Alzheimer's disease diagnosing system, comprising:

a video camera disposed so as to face a patient's eye;

illuminating means for irradiating a pulse of light in a predetermined cycle;

detecting means for detecting, at a plurality of time points, a value representing a pupil size based upon said video signal output from said video camera; and change rate calculating means for calculating a rate of change of said pupil size in at least one of said predetermined intervals between said time points on the basis of said values detected by said detecting means; and determination means for determining whether the patient is affected with Alzheimer's disease on the basis of said rate of change of the pupil size calculated by said change rate calculating means.

6. A pupil measuring system comprising:

a video camera disposed so as to face a patient's eye;

illuminating means for irradiating a pulse of infrared rays and for obtaining an image signal from said video camera in a predetermined cycle;

processing means for receiving an image signal obtained by said video camera and for generating a digital video signal from said image signal output by said video camera;

detecting means for detecting, at a plurality of time points, an area of the patient's pupil based upon said digital video signal;

control means for controlling said detecting means to detect said area of the patient's pupil a predetermined number of times;

mean value calculating means for calculating a mean value of detected area values of said pupil.

7. The pupil measuring system as claimed in claim 6, further comprising:

a visible light cut-off filter connected to said video camera.

8. An Alzheimer's disease diagnosing system comprising:

a video camera disposed so as to face a patient's eye;

illuminating means for irradiating a pulse of infrared rays and for obtaining an image signal from said video camera in a predetermined cycle;

processing means for receiving said image obtained by said video camera and for generating a digital video signal from said image signal output by said video camera;

detecting means for detecting an area of the patient's pupil based upon said digital video signal;

first control means for controlling said detecting means to detect said area of the patient's pupil at predetermined intervals;

mean value calculating means for calculating a mean value of detected area values of the patient's pupil obtained at said predetermined intervals;

second control means for controlling said first control means and said mean value calculating means to intermittently measure said mean value of said detected area values;

change rate calculating means for calculating a rate of change of said area of the patient's pupil based upon a plurality of said mean values; and determination means for determining whether the patient is affected with Alzheimer's disease based on said rate of change of the pupil area.

9. An Alzheimer's disease diagnosing system comprising:

a video camera disposed so as to face a patient's eye;

illuminating means for irradiating infrared rays and for obtaining an image signal from said video camera in a predetermined cycle;

processing means for receiving said image obtained by said video camera and for generating a digital video signal from said image signal output by said video camera;

detecting means for detecting an area of the patient's pupil based upon said digital video signal;

first control means for controlling said detecting means to detect said area of the patient's pupil at predetermined intervals;

mean value calculating means for calculating a mean value of detected area values of the patient's pupil obtained at said predetermined intervals;

second control means for controlling said first control means and said mean value calculating means to intermittently measure said mean values;

change rate calculating means for calculating a rate of change of said area of the patient's pupil based upon a plurality of said mean values;

determination means for determining whether the patient is affected with Alzheimer's disease based on said rate of change of the pupil area; and display means for displaying a graph indicating said mean values of the pupil area.

10. The Alzheimer's disease diagnosing system as claimed in claim 9, further comprising:

a visible light cut-off filter connected to said video camera.

11. An Alzheimer's disease diagnosing system as claimed in claim 9, wherein said display means simultaneously displays said graph indicating said mean values and an image of the patient's pupil.

12. An Alzheimer's disease diagnosing system comprising:

a video camera disposed so as to face a patient's eye;

illuminating means for illuminating the patient's eye;

detecting means for detecting, at a plurality of time points, a value representing a pupil size based upon said video signal output from said video camera;

mean value calculating means for obtaining a predetermined number of values respective representing the pupil size for said time points detected by said detecting means, and for calculating a mean value of said values;

change rate calculating means for calculating a rate of change of said pupil size between said time points on the basis of said mean values calculated by said mean value calculating means; and determination means for determining whether the patient is affected with Alzheimer's disease on the basis of said rate of change of the pupil size calculated by said change rate calculating means.

* * * * *